US 6,668,824 B1

(12) United States Patent
Isaza et al.

(10) Patent No.: US 6,668,824 B1
(45) Date of Patent: Dec. 30, 2003

(54) SYSTEM AND METHOD FOR ADJUSTABLE DISCONNECTION SENSITIVITY FOR DISCONNECTION AND OCCLUSION DETECTION IN A PATIENT VENTILATOR

(75) Inventors: Fernando J. Isaza, Carlsbad, CA (US); Stanley Wong, Rancho Santa Margarita, CA (US); Itzhak Verona, Carlsbad, CA (US); Peter Doyle, Vista, CA (US)

(73) Assignee: Nellcor Puritan Bennett Incorporated, Pleasanton, CA (US)

( * ) Notice: Subject to any disclaimer, the term of this patent is extended or adjusted under 35 U.S.C. 154(b) by 0 days.

(21) Appl. No.: 09/518,772

(22) Filed: Mar. 3, 2000

Related U.S. Application Data

(63) Continuation of application No. 09/198,994, filed on Nov. 23, 1998, now abandoned, which is a continuation of application No. 08/818,173, filed on Mar. 14, 1997, now Pat. No. 5,881,717.

(51) Int. Cl.[7] ............................................. A61M 16/00
(52) U.S. Cl. ........................... 128/202.22; 128/204.21; 128/204.23; 128/205.23
(58) Field of Search ..................... 128/200.24, 202.22, 128/204.21, 204.23, 205.23

(56) References Cited

U.S. PATENT DOCUMENTS

| | | | |
|---|---|---|---|
| 3,595,228 A | 7/1971 | Simon | 128/205.23 |
| 4,155,357 A | 5/1979 | Dahl | 128/202.22 |
| 4,176,617 A | 12/1979 | Pilipski | 128/202.22 |
| 4,286,589 A | 9/1981 | Thompson | 128/202.22 |
| 4,287,886 A | 9/1981 | Thompson | 128/202.22 |
| 4,550,726 A | 11/1985 | McEwen | 128/202.22 |
| 4,883,051 A | 11/1989 | Westenskow et al. | 128/204.21 |
| 5,057,822 A | 10/1991 | Hoffman | 128/202.22 |
| 5,320,092 A | 6/1994 | Ryder | 128/202.22 |
| 5,534,851 A | 7/1996 | Russek | 128/202.22 |
| 5,537,997 A | 7/1996 | Mechlenburg et al. | 128/204.23 |
| 5,626,129 A | 5/1997 | Klimm et al. | 128/205.23 |
| 5,662,099 A | 9/1997 | Tobia et al. | 128/202.22 |
| 5,715,812 A | 2/1998 | Deighan et al. | 128/204.23 |

(List continued on next page.)

FOREIGN PATENT DOCUMENTS

| | | |
|---|---|---|
| EP | 0 099 743 | 2/1984 |
| EP | 0 459 647 | 12/1991 |
| EP | 0 742 027 | 11/1996 |

OTHER PUBLICATIONS

International Search Report RE PCT/US98/03718 Dated Jun. 22, 1998.
Dräger—Evita Intensive Care Ventilator Instruction Manual.
Marketing Brochure—Pediatric–Adult Star 1500 Ventilator—Infrasonics, Inc. Star Products.

*Primary Examiner*—Aaron J. Lewis
(74) *Attorney, Agent, or Firm*—Fulwider Patton Lee & Utecht, LLP

(57) ABSTRACT

The system and method for detecting disconnection and occlusion of a tubing system of a patient ventilator detects disconnection of the tubing system, opens the exhalation valve, delivers an idle flow of breathing gas to the tubing system, disables breath triggering, and generates an alarm. A reconnection of the tubing system can also be detected, to initiate resumption of pressure supported inspiration. For occlusion detection, the pressure drop in the tubing system is determined by pressure sensors in the inspiratory and expiratory airways of the tubing system. The two pressure drop values are compared, and once occlusion is detected, an alarm is generated, and the ventilator responds to protect the patient from over distension. Abatement of the occlusion can also be monitored in a pressure based occlusion status cycling mode, and the ventilator can revert back to normal ventilation when either circuit occlusion or exhaust port occlusion are not detected.

26 Claims, 2 Drawing Sheets

U.S. PATENT DOCUMENTS

| | | | |
|---|---|---|---|
| 5,720,709 A | 2/1998 | Schnall | 128/204.23 |
| 5,740,796 A | 4/1998 | Skog | 128/204.23 |
| 5,743,253 A | 4/1998 | Castor et al. | 128/204.21 |
| 5,813,399 A | 9/1998 | Isaza et al. | 128/204.21 |
| 5,832,916 A | 11/1998 | Lundberg | 128/202.22 |
| 5,865,168 A | 2/1999 | Isaza | 128/204.21 |
| 5,881,717 A * | 3/1999 | Isaza | |
| 5,901,704 A * | 5/1999 | Estes et al. | 128/204.23 |
| 6,029,665 A * | 2/2000 | Berthon-Jones | 128/204.23 |
| 6,105,575 A * | 8/2000 | Estes et al. | 128/204.23 |
| 6,138,675 A * | 10/2000 | Berthon-Jones | 128/204.23 |
| 6,279,569 B1 * | 8/2001 | Berthon-Jones | 128/200.24 |
| 6,305,374 B1 * | 10/2001 | Zdrojkowski et al. | 128/204.21 |
| 6,360,741 B2 * | 3/2002 | Truschel | 128/202.22 |
| 6,390,091 B1 * | 5/2002 | Banner et al. | 128/204.21 |
| 6,392,555 B1 * | 5/2002 | Most, Jr. | 340/664 |

\* cited by examiner

SYSTEM AND METHOD FOR ADJUSTABLE DISCONNECTION SENSITIVITY FOR DISCONNECTION AND OCCLUSION DETECTION IN A PATIENT VENTILATOR

RELATED APPLICATIONS

This is a continuation of Ser. No. 09/198,994 filed Nov. 23, 1998, abandoned, which was a continuation of Ser. No. 08/818,173, filed Mar. 14, 1997, now U.S. Pat. No. 5,881,717.

BACKGROUND OF THE INVENTION

1. Field of the Invention

This invention relates generally to breathing ventilators, and more particularly relates to a pneumatically driven, electronically controlled ventilator system for providing breathing gas to a patient, and a method and system for detection of disconnection and occlusion in an airway of the ventilator system.

2. Description of Related Art

A patient receiving breath pressure support from a ventilator system typically receives breathing gas through a patient circuit of the ventilator. The patient circuit generally consists of two flexible conduits connected to a fitting called a patient wye. The free ends of the conduits are attached to the ventilator so that one conduit receives breathing gas from the ventilator's pneumatic system, and the other conduit returns gas exhaled by the patient to the ventilator. The volume of the exhaled gas may then be measured in a spirometer before it finally exits through an exhalation valve. The wye fitting is typically connected to the patient's breathing attachment or enclosure, which conducts breathing gas into the lungs, and exhaled gas from the lungs to the exhalation branch of the patient circuit. The pneumatic system at the inspiratory end of the patient circuit is typically closed before a breath, and the exhalation valve at the exhalation end of the patient circuit is typically preceded by a one-way valve, to prevent gas from flowing retrograde in the exhalation branch of the patient circuit.

Occurrences of low pressures in the exhalation limb of the patient's breathing gas circuit during the exhalation phase of the pressure supported breath can be a cause of concern for the patient unless they are carefully controlled. Pressures in the patient lung that fall below PEEP (Positive End Expiratory Pressure, a baseline pressure value) can impair a patient's lung function, and it can be important to maintain PEEP in a patient's lung to prevent collapse of the lung.

Disconnections of a patient breathing circuit can occur at the inspiratory limb, the expiratory limb, the patient circuit wye, or between the endotracheal tube and the patient wye. Patient breathing circuit disconnections result in the patient receiving either no breathing gas or very little gas from the ventilator, and can interfere severely with maintenance of PEEP. During ventilation, it is also desirable to be able to assess the state of the tubing system so that conditions such as kinked tubes and high resistance filters that can occlude the flow of breathing gas and interfere with maintenance of PEEP are detected, to prevent injury to the patient attached to the ventilator, and so that increases in the work of breathing are minimized. It is also important to detect an occlusion condition in which the exhalation valve is stuck closed. Therefore, it is important to be able to detect disconnections and occlusions and to alert the respiratory therapist to these conditions. The present invention meets these needs.

SUMMARY OF THE INVENTION

Briefly, and in general terms, the present invention provides for a system and method for detecting disconnection and occlusion of a tubing system in the patient circuit of a patient ventilator. Once a patient tubing disconnection has been determined, the ventilator can then open the exhalation valve, deliver an idle flow with 100% oxygen to the tubing system, disable breath triggering, and generate an alarm indicating disconnection. The system and method of the invention can also detect a reconnection of the tubing system, and initiate resumption of pressure supported inspiration. For occlusion detection, the pressure drop in the tubing system is determined by pressure sensors in the inspiratory and expiratory airways of the tubing system. The two pressure drop values are compared and a severe alarm will sound if the actual pressure drop exceeds the severe level. Once occlusion is detected, the ventilator can respond to protect the patient from over distension, and can monitor the tubing system for abatement of the occlusion in a pressure based occlusion status cycling mode. The ventilator can revert back to normal ventilation when either circuit occlusion or exhaust port occlusion are not detected.

In one currently preferred embodiment, the invention accordingly provides for a method for detecting disconnection or occlusion of a patient tubing system of a pneumatically driven, electronically controlled ventilator system for providing breathing gas to a patient during the exhalation phase of a breath cycle, the exhalation phase having a plurality of control intervals, with each of the control intervals having a predetermined duration. A method of the invention comprises the steps of delivering a flow of breathing gas to a patient during an inspiratory phase of a breath cycle, determining an onset of an exhalation phase of the breath cycle, suspending gas flow delivery to the patient tubing system during the exhalation phase of the breath cycle, and monitoring exhalation flow and pressure in the patient tubing system during a plurality of control intervals of the exhalation phase of the breath cycle to determine whether a condition indicating disconnection of the patient tubing system has occurred. The exhalation pressure in the patient tubing system is monitored during a plurality of control intervals of the exhalation phase of the breath cycle to determine whether a condition indicating occlusion of the patient tubing system has occurred; and a disconnection signal indicating disconnection of the patient tubing system is generated responsive to the exhalation flow and the pressure in the patient tubing system if the condition indicating occlusion of the patient tubing system has not occurred, and if the condition indicating disconnection of the patient tubing system has occurred.

In another currently preferred embodiment, the invention provides for a system for detecting disconnection or occlusion of a patient tubing system of a pneumatically driven, electronically controlled ventilator system for providing breathing gas to a patient during the exhalation phase of a breath cycle, the exhalation phase having a plurality of control intervals, with each of the control intervals having a predetermined duration. The system comprises means for delivering a flow of breathing gas to a patient during an inspiratory phase of a breath cycle, means for determining an onset of an exhalation phase of the breath cycle, means for suspending gas flow delivery to the patient tubing system during the exhalation phase of the breath cycle, and means for monitoring exhalation flow and pressure in the patient tubing system during a plurality of control intervals of the exhalation phase of the breath cycle to determine whether a condition indicating disconnection of the patient tubing system has occurred. The system may include means for monitoring exhalation pressure in the patient tubing system during a plurality of control intervals of the exhalation phase of the breath cycle to determine whether a condition indicating occlusion of the patient tubing system has occurred, and means for generating a disconnection signal indicating disconnection of the patient tubing system responsive to the exhalation flow and the pressure in the patient tubing system if the condition indicating occlusion of the patient tubing system has not occurred, and if the condition indicating disconnection of the patient tubing system has occurred.

In a presently preferred embodiment, a disconnection alarm signal is generated, the exhalation valve is opened, an idle flow is delivered, and flow and pressure are monitored to determine whether a condition indicating reconnection of the patient tubing system has occurred. In another currently preferred embodiment, the resumption of flow of breathing gas to the patient tubing system is initiated during an inspiratory phase of a breath cycle if a condition indicating reconnection of the patient tubing system has occurred.

The invention also provides for a method for detecting occlusion of a patient tubing system of a pneumatically driven, electronically controlled ventilator system for providing breathing gas to a patient during the exhalation phase of a breath cycle, the exhalation phase having a plurality of control intervals, each of the control intervals having a predetermined duration. A method of the invention comprises the steps of delivering a flow of breathing gas to a patient during an inspiratory phase of a breath cycle, determining an onset of an exhalation phase of the breath cycle, suspending gas flow delivery to the patient tubing system during the exhalation phase of the breath cycle, monitoring exhalation pressure in the patient tubing system during a plurality of control intervals of the exhalation phase of the breath cycle to determine whether a condition indicating occlusion of the patient tubing system has occurred; and generating a occlusion signal indicating occlusion of the patient tubing system responsive to the pressure in the patient tubing system if the condition indicating disconnection of the patient tubing system has occurred.

In another presently preferred embodiment, the invention provides for a system for detecting occlusion of a patient tubing system of a pneumatically driven, electronically controlled ventilator system for providing breathing gas to a patient during the exhalation phase of a breath cycle, the exhalation phase having a plurality of control intervals, with each of the control intervals having a predetermined duration. The system comprises means for delivering a flow of breathing gas to a patient during an inspiratory phase of a breath cycle, means for determining an onset of an exhalation phase of the breath cycle, means for suspending gas flow delivery to the patient tubing system during the exhalation phase of the breath cycle, means for monitoring exhalation pressure in the patient tubing system during a plurality of control intervals of the exhalation phase of the breath cycle to determine whether a condition indicating occlusion of the patient tubing system has occurred, and means for generating an occlusion signal indicating occlusion of the patient tubing system responsive to the pressure in the patient tubing system if the condition indicating occlusion of the patient tubing system has occurred.

In a presently preferred embodiment, the invention also provides for generation of an occlusion signal indicating occlusion of the patient tubing system if the condition indicating occlusion of the patient tubing system has occurred. In a currently preferred embodiment, an occlusion alarm signal is generated, the exhalation valve is opened, an idle flow is delivered, and flow and pressure are monitored in an occlusion status cycling mode to determine whether a condition indicating abatement of occlusion of the patient tubing system has occurred. The invention also provides for initiation of the resumption of flow of breathing gas to the patient tubing system during an inspiratory phase of a breath cycle if a condition indicating abatement of occlusion of the patient tubing system has occurred.

These and other aspects and advantages of the invention will become apparent from the following detailed description and the accompanying drawings, which illustrate by way of example the features of the invention.

DETAILED DESCRIPTION OF THE PREFERRED EMBODIMENTS

Figure 1:
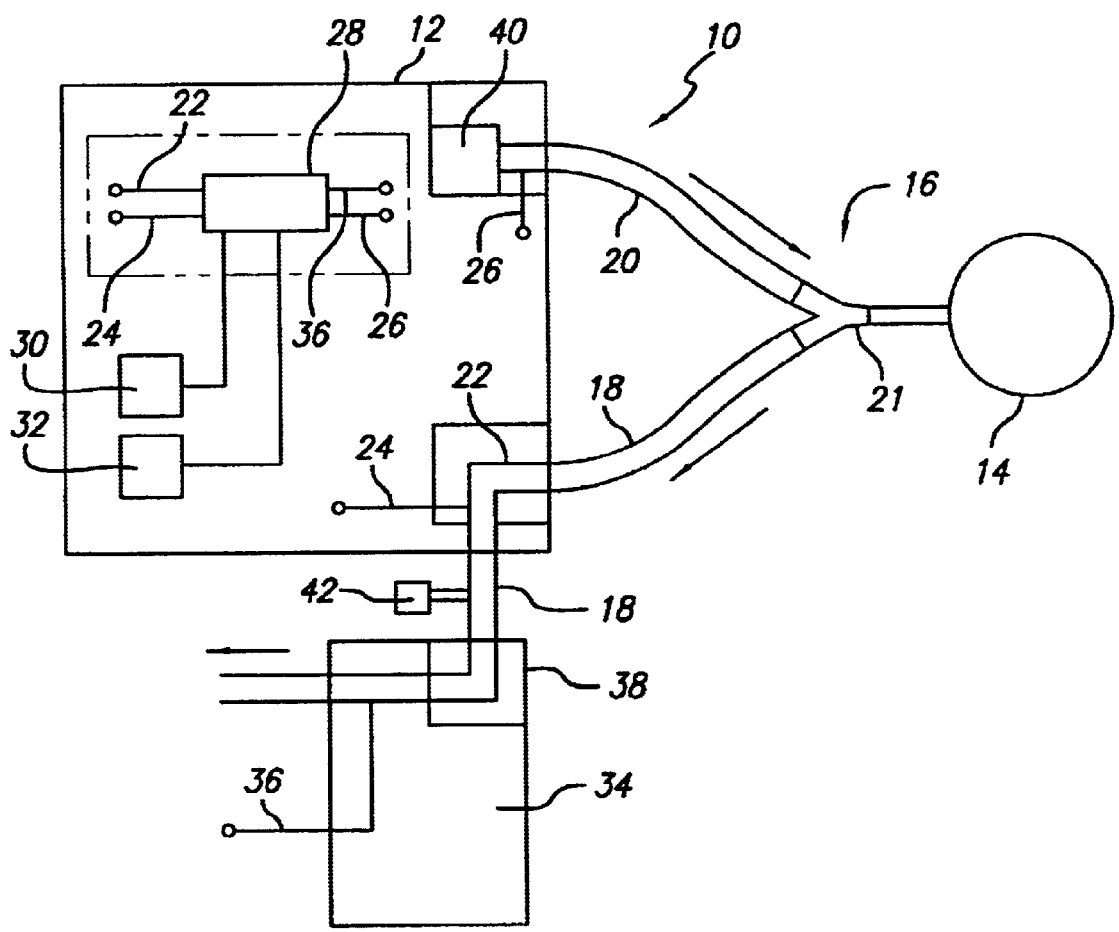
FIG. 1 is a schematic diagram of the system for detecting disconnection and occlusion of a patient tubing system for a patient ventilator, according to the invention.

Pressures in the tubing system of a patient ventilator can fall below a baseline pressure value during disconnections and occlusions of the tubing system, risking impairment of a patient's lung function, and possible collapse of the lung. Patient breathing circuit disconnections result in the patient receiving either no breathing gas or very little gas from the ventilator, and can interfere severely with maintenance of PEEP. Occlusions in the tubing system can also dangerously increase the work of breathing. It is therefore important to be able to detect disconnections and occlusions and to respond to these conditions.

As is illustrated in the drawings, which illustrate, by way of example, the invention, in a first embodiment, the invention provides for a method and system for detection of disconnection and occlusion of a patient tubing system of a pneumatically driven, electronically controlled ventilator system. Parameters used to detect patient tubing system disconnections include pressure and exhalation flow levels measured by the pressure and flow sensors located in the exhalation module during the first 200 msec of exhalation, the volume returned during the exhalation phase, the volume delivered during the previous inspiratory phase, and in pressure based ventilation, the desired flow level if the time limit is reached.

The system 10 for detecting disconnection and occlusion of the patient tubing system of a pneumatically driven, electronically controlled ventilator system 12 is illustrated schematically in FIG. 1. The patient 14 is connected by the tubing system 16 to receive breathing gas. The tubing system includes an exhalation line 18 and an inhalation line 20 connected to the patient by a patient wye 21. A pressure sensor 22 and a flow sensor 24 are connected to the exhalation line to monitor pressure and flow, respectively, of the breathing gas in the exhalation line, and a pressure sensor 26 is also connected to the inhalation line to monitor the pressure in the inhalation line. All inputs from the sensors are received by a microprocessor 28 which governs all of the microcomputer based functions of the ventilator system, and which controls activation of a disconnection alarm 30, and an occlusion alarm 32. The exhalation line is connected to an exhalation compartment 34, which also includes a pressure sensor 36 for monitoring pressure of breathing gas in the exhalation compartment. The ventilator system includes a pressure control valve 40 controlling pressure of breathing gas delivered to the patient, and a safety valve 42, typically connected to the exhalation line, for relieving excessive pressure of the breathing gas in the tubing system.

In a first set of criteria, a condition indicating disconnection of the patient tubing system has occurred can be declared if, during a control interval, the pressure in the tubing system as sensed by a pressure sensor in the exhalation line of the tubing system falls outside a desired, predetermined range, and exhalation flow is less than a desired, predetermined threshold, for a contiguous period of consecutive control intervals within a predetermined initial period of time following onset of an exhalation phase. In a preferred embodiment of the first set of criteria, the control interval is 5 msec., and all of the following three conditions must be met at some time during the first 200 msec. of an exhalation phase, for a contiguous period of 100 consecutive milliseconds:

If $Pat\_press(n) \geq -0.5$ cmH$_2$O

AND $Pat\_press(n) \leq 0.5$ cmH$_2$O

AND $Dry\_exh\_flow(n) \leq 0.5$ lpm where Pat_press(n) is the pressure in the tubing system as sensed by a pressure sensor in the exhalation line of the tubing system during a control interval, and Dry_exh_flow(n) is the exhalation flow as measured by the exhalation flow sensor, compensated for the breathing gas mix and for humidity in the gas to represent dry conditions. Typically, an estimated amount of water vapor flow is removed from the initial flow measurement from the exhalation flow sensor Exh_flow. Then, the remaining dry flow is compensated for the expected gas mix (N$_2$, O$_2$).

However, even if all of the above conditions of the first set of criteria are met, the declaration of the patient tubing system disconnection is preferably deferred until a period of time has elapsed, in which it can be determined whether occlusion of the tubing system has occurred. In a presently preferred embodiment, this delay period is about 300 msec following the onset of exhalation, independent of the breath phase. Detection of a tubing occlusion is allowed to be declared first, since it is possible for a tubing occlusion to falsely generate all the patient tubing system disconnection conditions of the first criteria.

Patient tubing system disconnections will usually be detected based on the flow seen by the exhalation flow sensor and the Pat_press level, during the first 200 msec of any exhalation. In the vast majority of cases, the Pat_press level will be at or near zero cmH$_2$O of pressure, and since no communication exists between the ventilator's inspiration and exhalation ports, no flow will be detected by the exhalation flow sensor.

In a second set of criteria, a condition indicating disconnection of the patient tubing system has occurred can be declared if the pressure in the tubing system as sensed during a control interval by a pressure sensor in the exhalation line of the tubing system falls outside a desired, predetermined range, and exhalation flow is less than a disconnection flow limit threshold based upon a flow target and a predetermined disconnection sensitivity, for a contiguous period of consecutive control intervals within a predetermined initial period of time following onset of an exhalation phase. In a preferred embodiment of the second set of criteria, the control interval is 5 msec., and all of the following three conditions must be met for a contiguous period of 10000 consecutive milliseconds, during the exhalation phase:

If $Pat\_press(n) \geq -0.5$ cmH$_2$O

AND $Pat\_press(n) \leq 0.5$ cmH$_2$O

AND $Dry\_exh\_flow(n) \leq disconnect\_flow\_limit$ where flow_target is the value of the ventilator's predetermined desired steady state flow delivery during the exhalation phase; disconnect_flow_limit is defined as flow_target*(1-disconnect_sensitivity/100), and if disconnect_flow_limit is less than 0.5 lpm, then disconnect_flow_limit is 0.5 lpm.

Disconnect_sensitivity is a setting, expressed in percent, that represents the percent of volume delivered in the previous inspiration, that was not returned (i.e, was lost) during the exhalation phase of the same breath. In a presently preferred embodiment, the range for disconnect_sensitivity is as follows:

$$20\% \leq disconnect\_sensitivity \leq 95\%$$

In the case of a disconnection at the patient circuit inspiratory limb it is possible for the patient to generate flows in excess of 0.5 lpm and pressures outside the ±0.5 cmH$_2$O range of the first set of criteria, but it is unlikely that these events will coincide with the first 200 msec of exhalation for long periods of time. This is the reason why the second set of criteria was developed.

When patient tubing system disconnections occur in a particular exhalation phase, they will usually be detected during a next exhalation, or if the disconnection does not cause autocycling of the ventilator, the disconnection can be detected during the current exhalation by the second set of criteria.

In a third set of criteria, a condition indicating disconnection of the patient tubing system has occurred can be declared if a desired flow target is greater than or equal to a maximum flow input to the flow controller, and the duration of a current inspiration is greater than or equal to a maximum allowed spontaneous inspiration time. This third set of criteria can be defined as follows:

If $Desired\_flow >= Flow\_cmd\_limit$

AND $Insp\_time >= Time\_limit$ where Insp_time is the duration of the current inspiration, Time_limit is the maximum allowed spontaneous inspiration time, and Flow_cmd_limit is the maximum flow input to the flow controller. For Pressure Based Ventilation (PBV), Flow_cmd_limit is dependent upon the patient type, and is typically 200 lpm for adult patients, and 80 lpm for pediatric patients.

The third set of criteria applies during the inspiration phase of a breath only, and only for spontaneous breaths, such as for Continuous Positive Airway Pressure (CPAP) or Pressure support, for example.

The third set of disconnection detection criteria reflects the fact that if a true disconnection occurs, during Pressure Based Ventilation (PBV), the desired flow will be driven to the maximum command limit if enough time is allowed. This type of response is guaranteed, even for the lowest pressure support level, if a total disconnection occurs at the beginning of the breath or during the previous exhalation, at any of the limbs or the endotracheal tube side of the wye. Thus this criteria fits very well for reconnection verification purposes, which will be discussed further below.

In a fourth set of criteria, a condition indicating disconnection of the patient tubing system has occurred can be declared if the exhalation volume is less than the integral of the net flow from the beginning of inspiration to the beginning of exhalation with respect to time, multiplied by a proportional factor and a disconnection sensitivity factor, for three consecutive breaths. The fourth criterion can be defined as follows:

Exh_vol<Insp_vol*proportional_factor*(1-disconnect_sensitivity/100)

for three (3) consecutive breaths
where:

$$Inspvol = -\int_{BeginInsp}^{BeginExhal} NetFlow * \frac{\delta t}{60} \quad \text{(Eq. 1)}$$

Exh_vol=Σ(Net_flow*δt/60) if Q_exh_finished=0; and proportional_factor is defined by the pseudo code below:
If EIP−SOIP≦0.1
  Then proportional_factor=0
  Else proportional_factor=(EIP−EEPUO)/(EIP−SOIP)
where EIP=End of inspiration pressure; $EEPU_0$=End of exhalation pressure unfiltered at the time Q_exh_finished is set to 1; and SOIP (start of inspiration pressure)=value of P_wye_unfiltered at the beginning of the current breath's inspiration.

P_wye_unfiltered is calculated using the equation:

P_wye_estimate$_n$=MAX (P_wye_insp_based_estimate$_n$, P_wye_exh_based_estimate$_n$);

where

P_wye_insp_based_estimate$_n$=Pat_press_insp_filtered$_n$− Ri*(Air_flow$_n$+O2_flow$_n$).

The term P_wye_exh_base_estimate$_n$ is defined by the pseudo code below:

```
If      Exh_flow < 150
        Then P_wye_exh_based_estimate_n = Pat_press_filtered_n
        - Re*Exh_flow_n
        Else P_wye_exh_based_estimate_n = Pat_press_filtered_n
        - Re*150
where:
        Ri = Ri_slope * (air_flow_n+O2_flow_n) + Ri_intercept
        Re = Re_slope * Exh_flow_n + Re_intercept
        Ri_slope =        Slope for the inspiratory limb
                          resistance equation
        Ri_intercept =    intercept for the inspiratory limb
                          resistance equation
        Re_slope =        Slope for the expiratory limb
                          resistance equation.
        Ri_intercept =    intercept for the expiratory limb
                          resistance equation.
```

Q_exh_finished is set to 0 (zero) at the beginning of exhalation and becomes 1 (one) the first time Net_flow_change_counter is greater than 20 AND at least 200 msec of exhalation have elapsed or if the exhalation phase ends, whichever occurs first. Once Q_exh_finished is set to 1, it remains in this state until the beginning of the next exhalation phase. Net_flow_change_counter is initialized to zero at the beginning of exhalation and incremented as indicated by the pseudo code below:

```
If      Abs(Net_flow_filtered_n − Net_flow_filtered_{n-1}) < 0.01
        * flow_target
```

```
-continued
AND     Net_flow ≦ 0.2 + 0.08 * flow_target
        Then    Net_flow_change_counter =
                        Net_flow_change_counter + 1
        Else Net_flow_change_counter = 0;
``` where:

flow_target=Value of the ventilator's predetermined desired steady state flow delivery during the exhalation phase. For pressure triggering mode the value for flow_target is 1 lpm (Purge_flow). For flow triggering mode the value is Base_flow.

n=control interval initialized to zero at the beginning of exhalation

Net_flow_filtered$_n$=Filtered Net_flow value. An alpha filter (α=0.9) is used to filter Net_flow.

Net_flow_filtered$_{-1}$=Net_flow of last inspiration interval.

Insp_vol is initialized to 0 (zero) at the beginning of inspiration. Exh_vol is initialized to zero at the beginning of exhalation. The inequality in the criteria is tested only once, and always during the interval where Q_exh_finished is set to 1.

The fourth set of criteria enables the ventilator to also detect disconnections at the patient side of the endotracheal tube, since the volume returned will be much less than the volume delivered during a previous inspiration. A detection threshold setting, used by the therapist, is incorporated in the fourth set of criteria to avoid false disconnection detections generated by leaks in the patient lungs or the tubing circuit. Three consecutive breaths are needed for the fourth set of criteria for declaration of disconnection to avoid false declarations when the patient "out-draws" the ventilator during volume ventilation.

Once any one set of criteria for declaring disconnection of the patient tubing system are met, the ventilator will open the exhalation valve, deliver an idle flow, such as typically a 5 lpm idle flow with 100% oxygen in the breathing gas mix, if possible, disable breath triggering, and generate an alarm indicating disconnection of the patient tubing.

Abatement of the condition of disconnection of the tubing system, or reconnection, will be detected when any one of the following conditions occurs:

1) If 80% of the idle flow is detected by the exhalation flow sensor as $Q_{exh}$ (the exhalation flow compensated to dry flow) for 500 consecutive milliseconds; or
2) When both $P_{insp}$ and $P_{exh}$ read less than −1.5 $cmH_2O$ for more than 100 consecutive milliseconds;
3) When both $P_{insp}$ and $P_{exh}$ read more than 1.0 $cmH_2O$ for more than 100 consecutive milliseconds; or
4) If $P_{insp}$ reads more than 10 $cmH_2O$ for more than 100 msec, consecutively.

Upon detection of a reconnection, the ventilator will initiate delivery of a pressure supported inspiration (PSI), and will return to normal ventilation, typically using the settings in effect prior to the patient tubing system disconnection, once the inspiration phase of the PSI is over. Typically, the ventilator system will check for disconnection of the tubing system from the beginning of the PSI until the end of the exhalation following the PSI using all but the fourth set of criteria, and then using all criteria thereafter.

In another currently preferred embodiment, the invention also provides for a method and system for dynamically monitoring the pressure drop of the tubing system (i.e.

including the patient airway tubing, bacteria filters, and humidifier system) of a pneumatically driven, electronically controlled ventilator system for providing breathing gas to a patient during the exhalation phase of a breath cycle, with the exhalation phase having a plurality of control intervals, and each of the control intervals having a predetermined duration, for increases in pressure drop due to occlusions in the tubing system. Those skilled in the art will recognize that the predetermined duration of the control intervals may be fixed, and will also recognize that it may be advantageous to vary the control intervals according to sampling criteria established during operation of the ventilator, based upon performance of the ventilator while ventilating the patient. During ventilation, the pressure drop for a severe occlusion is computed based on the tubing type obtained, the delivered flows and the exhaled flows. The actual pressure drop is determined by comparing the pressure drop values from the inspiratory and expiratory pressure sensors, and an alarm indicating severe occlusion will be generated if the actual pressure drop exceeds a predetermined severe threshold level. The ventilator monitors the occlusion in a pressure based occlusion status cycling mode. This mode serves to protect the patient from over distension and to determine if the severe occlusion abates. The ventilator reverts back to normal ventilation when either tubing circuit occlusion or exhaust port occlusion are not detected.

The tubing pressure drop mathematical model ($dP_{model}$) can be expressed by a quadratic equation with flow as the independent variable, as follows:

$$dP_{model} = A*Q^2 + B*Q + C \quad \text{(Eq. 2)}$$

where A, B, C are constants and Q is the flow through the tubing. The constant C is zero since dP is zero when Q is zero. Therefore Eq. 2 becomes $$dP_{model} = A*Q^2 + B*Q \quad \text{(Eq. 3)}$$

The remaining coefficients, A and B, can be obtained using a straight line fit of $dP_{model}/Q$:

$$dP_{model}/Q = A*Q + B \quad \text{(Eq. 4)}$$

where A and B are constants to the straight line fit.

The quadratic pressure drop model (Eq. 3) is valid only for static measurements in flows. For dynamic flow rates, some errors are encountered in this model; but the model still serves as a good approximation of the pressure drop as a function of flow.

The actual or measured tubing circuit pressure drop, dP, is the difference between the inspiratory pressure sensor reading, $P_{insp}$, and the expiratory reading, $P_{exh}$:

$$dP = P_{insp} - P_{exh} \quad \text{(Eq. 5)}$$

For occlusion detection purposes Eq. 5 is modified to account for the pressure and low sensor accuracies (i.e. offset & gain drift). The determination of dP is thus typically adjusted for such factors as offset and gain drift, based upon the following equation:

$$dP_{meas} = (P_{insp} - P_{exh}) - (0.7 + Abs(P_{insp})*0.062) \quad \text{(Eq. 6)}$$

The pressure drop threshold for a severe occlusion is dependent upon the tubing classification as either adult or pediatric. Thus the pressure drop threshold for a severe occlusion, $dP_{severe}$, is defined for an adult patient by:

$$dP_{severe} = 0.005*Q^2 + 0.1491*Q + 0.0142 \quad \text{(Eq. 7)}$$

and for a pediatric patient by:

$$dP_{severe} = 0.0082*Q^2 + 0.1431*Q + 0.0136 \quad \text{(Eq. 8)}$$

where Q is the flow in lpm causing the pressure drop to rise to a severe level. Since the location of the pressure drop increase is unknown, the maximum flow between $Q_{insp}$ and $Q_{exh}$ is used:

$$Q = \max[Q_{insp}, Q_{exh}] \quad \text{(Eq. 9)}$$

The threshold $dP_{severe}$ is typically limited to a minimum value of 5 cmH$_2$O to prevent false triggering of the alarm due to the usage of a Cascade Humidifier or due to the presence of water in the tubing circuit, and typically is limited to a maximum of 100 cmH$_2$O, since 100 cmH$_2$O is typically the maximum set wye pressure.

The actual or measured tubing circuit pressure drop, and the pressure drop threshold for a severe occlusion, $dP_{severe}$, for either an adult patient or a pediatric patient, is determined in every 5 ms cycle and are compared. If the measured pressure drop exceeds the pressure drop threshold for a severe occlusion for the prescribed durations discussed below, a severe occlusion alarm is annunciated and ventilation switches to an occlusion status cycling mode, discussed further below.

In one currently preferred embodiment, three independent time counters are used to monitor violations of a severe occlusion threshold depending on the magnitude of $dP_{meas}$. A violation occurs when $dP_{meas}$ exceeds the threshold $dP_{severe}$. The three time counters are associated to $dP_{meas}$ values that fall in the pressure ranges of >20, >10, and >5 cmH$_2$O respectively. Each counter is individually incremented if a violation occurs and if $dP_{meas}$ is greater than the corresponding pressure range. If the condition for each counter is not met, then the counter is reset. Once the counters exceed 10, 20, and 40 cycles (i.e., for 50, 100, or 200 consecutive milliseconds) respectively, a severe occlusion alarm is annunciated.

The following pseudo code implements the above algorithm:

```
if (dP_meas > dP_severe)
{
    if (dP_meas > 20)
        t_20_cm = t_20_cm + 1 ;
    else
        t_20_cm = 0 ;
    if (dP_meas > 10)
        t_10_cm = t_10_cm + 1 ;
    else
        t_10_cm = 0 ;
    if (dP_meas > 5)
        t_5_cm = t_5_cm + 1 ;
    else
        t_5_cm = 0 ;
}
else
{
    t_5_cm = 0 ;
    t_10_cm = 0 ;
    t_20_cm = 0 ;
}
if (t_5_cm > 40 OR t_10_cm > 20 OR t_20_cm > 10)
    severe_occlusion_detected = 1 ;
```

Occlusion of the exhalation exhaust port can also be detected from increases in the pressure drop of the exhalation compartment. The exhalation compartment includes those portions of the conduit downstream of the exhalation pressure transducer, including the heater manifold, flow sensor, exhalation valve, and any tubing attached to the exhalation outlet port. The amount of increase in pressure drop for the exhalation compartment is the same for a severe occlusion defined for adult patients. This increase is typically given by $$P_{increase} = 0.005*Q^2 + 0.1491*Q + 0.0142 \quad (Eq.\ 10)$$

where $Q = Q_{exh}$

The exhaust port pressure threshold, $P_{exhaust\_port\_thresh}$, is calculated as the pseudo code below indicates.

If $P_{increase} < 1$

Then $$P_{exhaust\_port\_thresh} = 7.35 + PEEP + P_{exh}*0.03 \quad (Eq.\ 11)$$

Else $$P_{exhaust\_port\_thresh} = P_{increase} + PEEP + P_{exh}*0.03 + 6.35 \quad (Eq\ 12)$$

where $P_{exhaust\_port\_thresh}$ has an upper bound of 100 cmH$_2$O.

The exhalation pressure sensor measurement, $P_{exh}$, is compared to $P_{exhaust\_port\_thresh}$. If $P_{exh} > P_{exhaust\_port\_thresh}$, for 100 consecutive milliseconds, and 200 msec have elapsed in the exhalation phase, a severe occlusion alarm is annunciated and ventilation switches to the occlusion status cycling mode. It is commonly difficult to detect this type of occlusion during inspiration, and this mode of occlusion detection is disabled during exhalation pauses.

The maximum flow delivered from the ventilator is dependent upon patient type. The maximum flow limits (Flow_cmd_limit) for adult and pediatric patients are typically 200 and 80 lpm, respectively.

In a presently preferred embodiment, concurrently with the declaration of severe occlusion or the detection of exhalation exhaust port occlusion, the invention provides for a pressure-based occlusion status cycling mode. Occlusion status cycling serves two objectives: 1) protecting the patient from over distension while attempting to ensure that the patient receives some ventilation, and 2) monitoring the inspiratory and expiratory phases to determine if the severe occlusion abates. As occlusion status cycling ensues, the severe occlusion may relax to either a partial or a normal state. If an occlusion does abate, it must qualify as less than a severe before the ventilator system will revert to settings in effect prior to the patient tubing system occlusion. During occlusion status cycling, a purge flow is not to be established.

Figure 2:
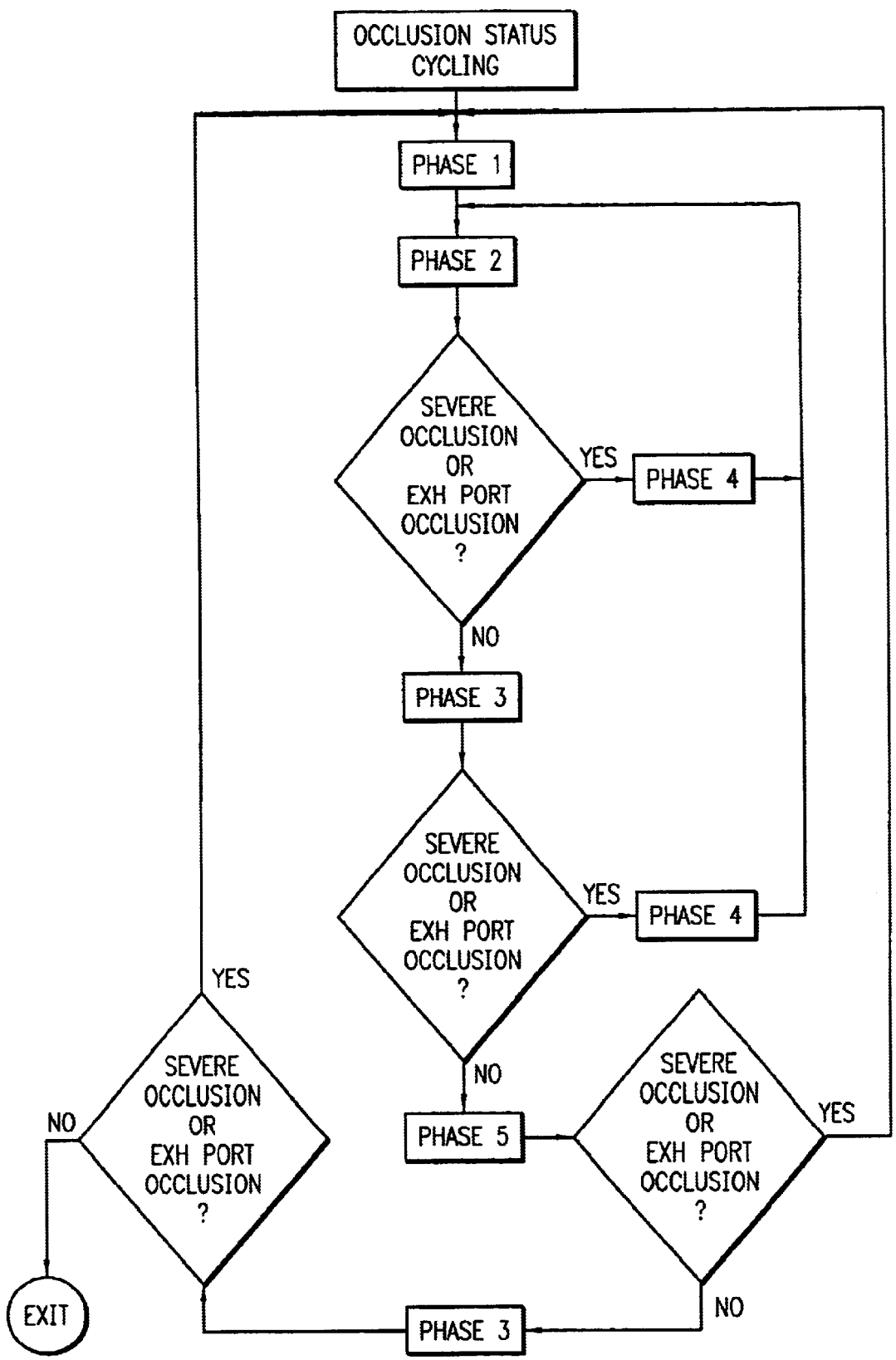
FIG. 2 is a flow chart illustrating the occlusion status cycling mode of the system of the invention.

Referring to FIG. 2, the flow chart depicts the sequence of events that must be performed for the implementation of occlusion status cycling. Five phases of occlusion status cycling have been defined for the purpose of flow charting.

Phase 1: An exhalation phase in which the ventilator closes the pressure solenoid valves, controls the expiratory valve to zero PEEP, discontinues flow triggering, sets PEEP equal to zero, sets the breathing gas oxygen percentage to 100, and opens the safety valve. This shut-down state persists until $P_{insp} < 5$ cmH$_2$O or until 15 seconds have elapsed, whichever occurs first. This phase is typically entered if an occlusion is detected while ventilating with normal settings.

Phase 2: An inspiration phase, in which at the beginning the ventilator closes the safety valve. After the 500 msec have elapsed, to allow for safety valve closure, the ventilator system delivers a Pressure Controlled Ventilation (PCV) based breath with an inspiratory pressure target of 15 cmH$_2$O, a flow acceleration percent of 100, an inspiratory time of (2500 −500) msec., and using $P_{insp}$ as the feedback signal for control.

Phase 3: An exhalation phase, in which the ventilator closes the pressure solenoid valves and controls the exhalation valve to zero PEEP. Exhalation will last until ($P_{insp} < 5$ cmH$_2$O AND at least 2.5 sec have passed) OR a total of 5 seconds have elapsed since the beginning of the exhalation.

Phase 4: An exhalation phase, in which the ventilator closes the pressure solenoid valves, controls the exhalation valve to zero PEEP and opens the safety valve. Exhalation will last until ($P_{insp} < 5$ cmH$_2$O AND at least 2.5 sec have passed) OR a total of 5 secs. have elapsed since the beginning of the exhalation Phase 5: An inspiration phase with current mandatory settings, the only exception being PEEP which remains at zero. $P_{exh}$ is used as the feedback signal for control purposes if the breathing algorithm is pressure based.

It will be apparent from the foregoing that while particular forms of the invention have been illustrated and described, various modifications can be made without departing from the spirit and scope of the invention. Accordingly, it is not intended that the invention be limited, except as by the appended claims.

What is claimed is:

1. A method for detecting disconnection of patient tubing of a pneumatically driven, electronically controlled ventilator system for providing breathing gas to a patient, the ventilator system having a breath cycle including an inspiratory phase and an exhalation phase, with a plurality of control intervals being established for the inspiratory phase and the exhalation phase, comprising the steps of:

determining an onset of the exhalation phase of the breath cycle;

monitoring exhalation flow and exhalation pressure in the patient tubing during a plurality of the control intervals of the exhalation phase; and determining whether a condition indicating possible disconnection of the patient tubing has occurred if, for a contiguous predetermined period of consecutive control intervals of the exhalation phase immediately following the onset of the exhalation phase, the exhalation pressure is within a predetermined range about zero, and if exhalation flow is less than or equal to a predetermined flow threshold.

2. The method of claim 1, wherein said contiguous predetermined period of consecutive control intervals of the exhalation phase immediately following the onset of the exhalation phase is about 200 msec.

3. The method of claim 1, wherein said predetermined flow threshold is a disconnection flow limit threshold based upon a flow target and a predetermined disconnection sensitivity.

4. The method of claim 3, wherein said contiguous predetermined period of consecutive control intervals of the exhalation phase immediately following the onset of the exhalation phase is about 10,000 msec.

5. The method of claim 1, further comprising the step of determining whether occlusion of the patient tubing has occurred.

6. The method of claim 5, further comprising the step of generating a disconnection signal indicating disconnection of the patient tubing if said condition indicating possible disconnection of the patient tubing system has occurred, and if occlusion of the patient tubing system has not occurred.

7. The method of claim 6, wherein said ventilator includes an exhalation valve, and when said disconnection signal is generated, further comprising the steps of opening the exhalation valve, delivering an idle flow of breathing gas, and generating an alarm indicating disconnection of the patient tubing responsive to said disconnection signal.

8. A method for detecting disconnection of patient tubing of a pneumatically driven, electronically controlled ventilator system for providing breathing gas to a patient, the ventilator system having a breath cycle including an inspiratory phase and an exhalation phase, with a plurality of control intervals being established for the inspiratory phase and the exhalation phase, comprising the steps of:

delivering a flow of breathing gas to a patient during the inspiratory phase of a breath cycle;

monitoring a desired flow target and the duration of the inspiratory phase;

generating a disconnection signal indicating disconnection of the patient tubing if, at the end of the inspiratory phase, the desired flow target is greater than or equal to a maximum flow threshold, and if the duration of a current inspiration is greater than or equal to a maximum allowed spontaneous inspiration time.

9. A method for detecting disconnection of patient tubing of a pneumatically driven, electronically controlled ventilator system for providing breathing gas to a patient, the ventilator system having a breath cycle including an inspiratory phase and an exhalation phase, with a plurality of control intervals being established for the inspiratory phase and the exhalation phase, comprising the steps of:

delivering a desired inspiratory flow of breathing gas to a patient during the inspiratory phase of the breath cycle;

determining an inspiratory volume of breathing gas delivered to the patient;

determining an adjusted inspiratory volume by multiplying said inspiratory volume of breathing gas by a proportional factor and a disconnection sensitivity factor;

determining an exhalation volume of breathing gas; and declaring disconnection of the patient tubing system has occurred if said exhalation volume is less than said adjusted inspiratory volume.

10. A system for detecting disconnection of patient tubing of a pneumatically driven, electronically controlled ventilator system for providing breathing gas to a patient, the ventilator system having a breath cycle including an inspiratory phase and an exhalation phase, with a plurality of control intervals being established for the inspiratory phase and the exhalation phase, comprising:

means for determining an onset of the exhalation phase of the breath cycle;

means for monitoring exhalation flow and exhalation pressure in the patient tubing during a plurality of the control intervals of the exhalation phase; and means for determining whether a condition indicating possible disconnection of the patient tubing has occurred if, for a contiguous predetermined period of consecutive control intervals of the exhalation phase immediately following the onset of the exhalation phase, the exhalation pressure is within a predetermined range about zero, and if exhalation flow is less than or equal to a predetermined flow threshold.

11. The system of claim 10, wherein said contiguous predetermined period of consecutive control intervals of the exhalation phase immediately following the onset of the exhalation phase is about 200 msec.

12. The system of claim 10, wherein said predetermined flow threshold is a disconnection flow limit threshold based upon a flow target and a predetermined disconnection sensitivity.

13. The system of claim 12, wherein said contiguous predetermined period of consecutive control intervals of the exhalation phase immediately following the onset of the exhalation phase is about 10,000 msec.

14. The system of claim 10, further comprising means for determining whether occlusion of the patient tubing has occurred.

15. The system of claim 14, further comprising means for generating a disconnection signal indicating disconnection of the patient tubing if said condition indicating possible disconnection of the patient tubing system has occurred, and if occlusion of the patient tubing system has not occurred.

16. The system of claim 15, wherein said ventilator includes an exhalation valve, and further comprising means for opening the exhalation valve, delivering an idle flow of breathing gas, and generating an alarm indicating disconnection of the patient tubing responsive to said disconnection signal.

17. A system for detecting disconnection of patient tubing of a pneumatically driven, electronically controlled ventilator system for providing breathing gas to a patient, the ventilator system having a breath cycle including an inspiratory phase and an exhalation phase, with a plurality of control intervals being established for the inspiratory phase and the exhalation phase, comprising the steps of:

means for delivering a flow of breathing gas to a patient during the inspiratory phase of a breath cycle;

means for monitoring a desired flow target and the duration of the inspiratory phase;

means for generating a disconnection signal indicating disconnection of the patient tubing if, at the end of the inspiratory phase, the desired flow target is greater than or equal to a maximum flow threshold, and if the duration of a current inspiration is greater than or equal to a maximum allowed spontaneous inspiration time.

18. A system for detecting disconnection of patient tubing of a pneumatically driven, electronically controlled ventilator system for providing breathing gas to a patient, the ventilator system having a breath cycle including an inspiratory phase and an exhalation phase, with a plurality of control intervals being established for the inspiratory phase and the exhalation phase, comprising the steps of:

means for delivering a desired inspiratory flow of breathing gas to a patient during the inspiratory phase of the breath cycle;

means for determining an inspiratory volume of breathing gas delivered to the patient;

means for determining an adjusted inspiratory volume by multiplying said inspiratory volume of breathing gas by a proportional factor and a disconnection sensitivity factor;

means for determining an exhalation volume of breathing gas; and means for declaring disconnection of the patient tubing system has occurred if said exhalation volume is less than said adjusted inspiratory volume.

19. A method for detecting occlusion of patient tubing of a pneumatically driven, electronically controlled ventilator system for providing breathing gas to a patient, the ventilator system having a breath cycle including an inspiratory phase and an exhalation phase, with a plurality of control intervals being established for the inspiratory phase and the exhalation phase, comprising the steps of:

monitoring exhalation pressure in the patient tubing;

monitoring inspiratory pressure in the patient tubing;

comparing the exhalation pressure and inspiratory pressure to determine a patient tubing pressure drop;

comparing said patient tubing pressure drop with a predetermined pressure drop threshold to determine whether a condition indicating occlusion of the patient tubing system has occurred.

20. The method of claim 19, wherein said ventilator system includes a plurality of counters, each of said counters having a different limit corresponding to a different respective pressure drop range, and said step of comparing said patient tubing pressure drop and said pressure drop threshold comprises comparing said patient tubing pressure drop and said pressure drop threshold in a plurality of consecutive control intervals, and incrementing each of said plurality of counters if the pressure drop is greater than the corresponding pressure range of the plurality of counters, respectively, and generating an alarm if the respective limits of any of said plurality of counters are exceeded.

21. The method of claim 19, further comprising the step of generating an occlusion alarm signal indicating occlusion of the patient tubing if said condition indicating occlusion of the patient tubing has occurred.

22. A system for detecting occlusion of patient tubing of a pneumatically driven, electronically controlled ventilator system for providing breathing gas to a patient, the ventilator system having a breath cycle including an inspiratory phase and an exhalation phase, with a plurality of control intervals being established for the inspiratory phase and the exhalation phase, comprising:

means for monitoring exhalation pressure in the patient tubing;

means for monitoring inspiratory pressure in the patient tubing;

means for comparing the exhalation pressure and inspiratory pressure to determine a patient tubing pressure drop; and means for comparing said patient tubing pressure drop with a predetermined pressure drop threshold to determine whether a condition indicating occlusion of the patient tubing system has occurred.

23. The system of claim 22, wherein said ventilator system includes a plurality of counters, each of said counters having a different limit corresponding to a different respective pressure drop range, and said means for comparing said patient tubing pressure drop and said pressure drop threshold comprises comparing said patient tubing pressure drop and said pressure drop threshold in a plurality of consecutive control intervals, means for incrementing each of said plurality of counters if the pressure drop is greater than the corresponding pressure range of the plurality of counters, respectively, and means for generating an alarm if the respective limits of any of said plurality of counters are exceeded.

24. The system of claim 22, further comprising means for generating an occlusion alarm signal indicating occlusion of the patient tubing if said condition indicating occlusion of the patient tubing has occurred.

25. A method for detecting occlusion of patient tubing of a pneumatically driven, electronically controlled ventilator system for providing breathing gas to a patient, the ventilator system having a breath cycle including an inspiratory phase and an exhalation phase, with a plurality of control intervals being established for the inspiratory phase and the exhalation phase, and the patient tubing including an exhalation compartment, comprising the steps of:

determining an onset of an exhalation phase of said breath cycle;

monitoring exhalation pressure in the exhalation compartment during a plurality of control intervals of said exhalation phase of said breath cycle; and generating an occlusion signal if said pressure in the exhalation compartment exceeds a predetermined exhaust port threshold pressure for a predetermined number of consecutive control intervals within a predetermined period of time during an exhalation phase.

26. A system for detecting occlusion of patient tubing of a pneumatically driven, electronically controlled ventilator system for providing breathing gas to a patient, the ventilator system having a breath cycle including an inspiratory phase and an exhalation phase, with a plurality of control intervals being established for the inspiratory phase and the exhalation phase, and the patient tubing including an exhalation compartment, comprising:

means for determining an onset of an exhalation phase of said breath cycle;

means for monitoring exhalation pressure in the exhalation compartment during a plurality of control intervals of said exhalation phase of said breath cycle; and means for generating an occlusion signal if said pressure in the exhalation compartment exceeds a predetermined exhaust port threshold pressure for a predetermined number of consecutive control intervals within a predetermined period of time during an exhalation phase.

* * * * *